(12) United States Patent
Suzman

(10) Patent No.: US 8,202,286 B1
(45) Date of Patent: Jun. 19, 2012

(54) ANATOMICALLY CORRECT TONGUE SCRAPING TOOL AND METHOD OF USE

(76) Inventor: Colin Suzman, Irvine, CA (US)

( * ) Notice: Subject to any disclaimer, the term of this patent is extended or adjusted under 35 U.S.C. 154(b) by 95 days.

(21) Appl. No.: 12/725,757

(22) Filed: Mar. 17, 2010

(51) Int. Cl.
*A61B 17/24* (2006.01)
(52) U.S. Cl. ........................................ 606/161
(58) Field of Classification Search .......... 606/161; 601/141, 142; 15/167.1, 167.2; D24/146, D24/147, 148, 149
See application file for complete search history.

(56) References Cited

U.S. PATENT DOCUMENTS

| | | |
|---|---|---|
| 3,890,964 A | 6/1975 | Castanedo |
| D367,707 S | 3/1996 | Baker |
| 5,947,912 A | 9/1999 | Montagnino |
| 6,440,149 B1 | 8/2002 | Potti |
| 2006/0010628 A1 * | 1/2006 | Moskovich ............ 15/111 |
| 2006/0052805 A1 * | 3/2006 | Cwik ..................... 606/161 |

* cited by examiner

*Primary Examiner* — Ryan Severson
*Assistant Examiner* — Jonathan W Miles
(74) *Attorney, Agent, or Firm* — Patent Law & Venture Group; Gene Scott

(57) ABSTRACT

An anatomically correct tongue scraping tool has a blade holder mounted at one end of an elongated handle and a replaceable blade selectively and rigidly engaged within the blade holder. A scraping portion of the blade extends outwardly from the blade holder and terminates with a smoothly integrated curvilinear edge having curve segments including: two spaced apart, concave segments, a convex segment, and two spaced apart, approximately circular segments which join the curvilinear edge with sides of the blade, wherein, the convex segment separates the concave segments and is positioned medially on the curvilinear edge.

5 Claims, 3 Drawing Sheets

ANATOMICALLY CORRECT TONGUE SCRAPING TOOL AND METHOD OF USE

BACKGROUND OF THE INVENTION

1. Field of the Present Disclosure

This disclosure relates generally to scrapers, peelers and other manual surface conditioning instruments and more particularly to a scraping device for cleaning the top surface of the human tongue.

2. Description of Related Art including information disclosed under 37 CFR 1.97 and 1.98

Castanedo, U.S. Pat. No. 3,890,964 provides a good understanding of the top surface of the tongue and ways in which it can become infested by microorganisms and thereby produce an exhaled breath odor that is anti-social. This patent discloses a single concave blade having a sharp edge, mounted on an elongate handle, the blade having a swept back curvature. Potti, U.S. Pat. No. 6,440,149 discloses a pair of spaced apart convex blades mounted on a handle, the blades formed with similar swept back curvature, a leading one of the blades being smooth and blunt, a second blade also blunt and having a rasp-like texture. Montagnino, U.S. Pat. No. 5,947,912 discloses a single, swept back, concave, blunt blade mounted on a vibratory handle. Adedokun discloses a generally flat, pointed, and sweptback blade with opposing ends having broad curvature; all mounted on a handle. Baker, Des. 367707 discloses a design for a straight flat and sharply pointed blade held by a handle. Other references were found to be in the same field as the present invention, but were considered too distinct in their structure to be considered relevant to the invention.

The related art described above discloses tongue scraping blades mounted on handles and intended for being positioned laterally on the tongue and moved manually by the handle so as to be drawn from a rear position on the top surface of the tongue toward the tip of the tongue. However, the prior art fails to take into account, the anatomical structure of the tongue, variations in tongue elasticity across the tongue's surface, ease of damage to the tongue's surface by relatively sharp blades, and comfort and convenience to those using such tongue cleaners. The present disclosure distinguishes over the prior art providing heretofore unknown structural features resulting in advantages as described in the following summary.

BRIEF SUMMARY OF THE INVENTION

Castanedo, U.S. Pat. No. 3,890,964 discloses the reasons for cleaning the tongue's top surface regularly. To accommodate this cleaning, the present invention is an anatomically correct tongue scraping tool having a blade holder mounted at one end of an elongated handle and a replaceable blade selectively and rigidly engaged within the blade holder. A scraping portion of the blade extends outwardly from the blade holder and terminates with a smoothly integrated curvilinear edge across the blade, the edge having curve segments including: two spaced apart, concave segments, a convex segment, and two spaced apart, approximately circular segments which join the curvilinear edge with sides of the blade, wherein, the convex segment separates the concave segments and is positioned medially on the curvilinear edge. This arrangement is ideal for fitting the transverse contour of the tongue and is therefore highly effective in removing plaque, bacteria, food particles and other causes of unsocial breath exhalent.

A primary objective inherent in the above described apparatus and method of use is to provide advantages not taught by the prior art.

Another objective is to provide a tongue scraper that is ergonomically suitable for matching the contour of the top surface of the tongue which is established by intrinsic muscles within the tongue.

A further objective is to provide a tongue scraper that has an edge finished with a circular radius so as to prevent the possibility of cutting or slicing into the tongue's surface.

A further objective is to provide a tongue scraper that has rounded blade corners so as to prevent the possibility of scratching the tongue's surface.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawings) is at least one of the best mode embodiments of the present invention In such drawing(s):

DETAILED DESCRIPTION OF THE INVENTION

The above described drawing figures illustrate the apparatus and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Figure 1:
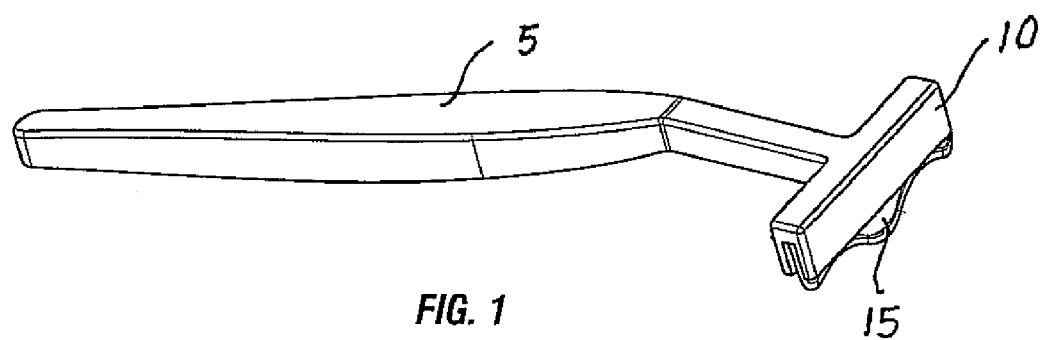
FIG. 1 is a perspective view of the invention showing a handle, a blade holder and a blade engaged within the blade holder.
Figure 2:
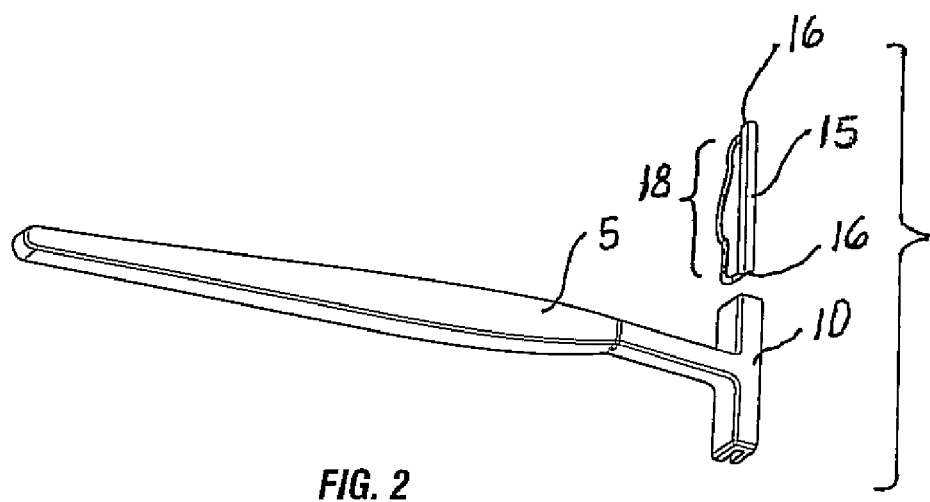
FIG. 2 is a similar perspective view of the invention showing the blade in a position lateral to the blade holder for being engaged with the blade holder, the rear surface of the blade being visible from an oblique angle.

The present invention, referred to herein simply by the term "invention," will now be described in detail. This description will additionally describe the method of use of the invention. The invention, in its preferred embodiment, is an anatomically correct tongue scraping tool comprising a blade holder 10 mounted at one end of an elongated handle 5 as shown in FIGS. 1 and 2. A planar blade 15 is selectively and rigidly engaged with the blade holder 10 so that a scraping portion 18 of blade 15 extends outwardly from the blade holder 10, terminating with a smoothly integrated curvilinear edge which preferably extends across the entire width of blade 15 between its sides 16 which are shown in FIG. 2.

Figure 3:
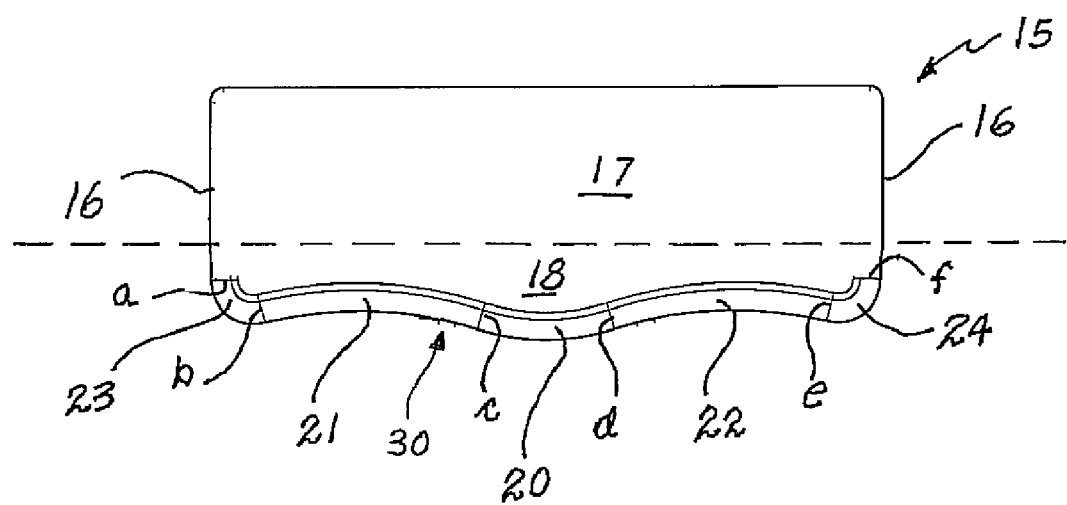
FIG. 3 is a front elevational view of the blade.

Blade 15 is approximately rectangular in shape and is relatively thin. As seen in FIG. 3, the scraping portion 18 terminates with a curvilinear edge preferably comprising a set of curved segments. These curved segments are clearly defined in FIG. 3 as extensive between short reference lines: a, b, c, d, e and f. Of the curved segments, two concave elements 21 and 22, are mirror images of each other and are positioned between a medial convex segment 20. The descriptive terms "concave" and "convex" are to be taken relative to the planar sides 16 and face surface 17 of blade 15. Describing the curvilinear edge further, two spaced apart, approximately circularly shaped, segments 23 and 24 are also mirror images of each other in shape, and these join the concave segments 21, 22 with the opposing sides 16 of the blade 15. As shown in FIG. 3, the curvilinear edge is formed by a contiguous arrangement across the blade 15 from left to right, of the edge segments: 23, 21, 20, 22, and 24. There is no juncture between any of these segments, but rather they form one smooth continuous curve and these segments are identified here as individual entities merely to draw attention to their specific shapes and relative positions; and, as will be shown, how these segments function to achieve the objectives of this invention. It should be noted that the convex segment 20 is medially positioned on the scraping portion 18, while, as said, the two concave segments 21 and 22 are positioned on either side of convex segment 20. This arrangement is critical to the successful operation of the tool as will be shown.

Figure 5:
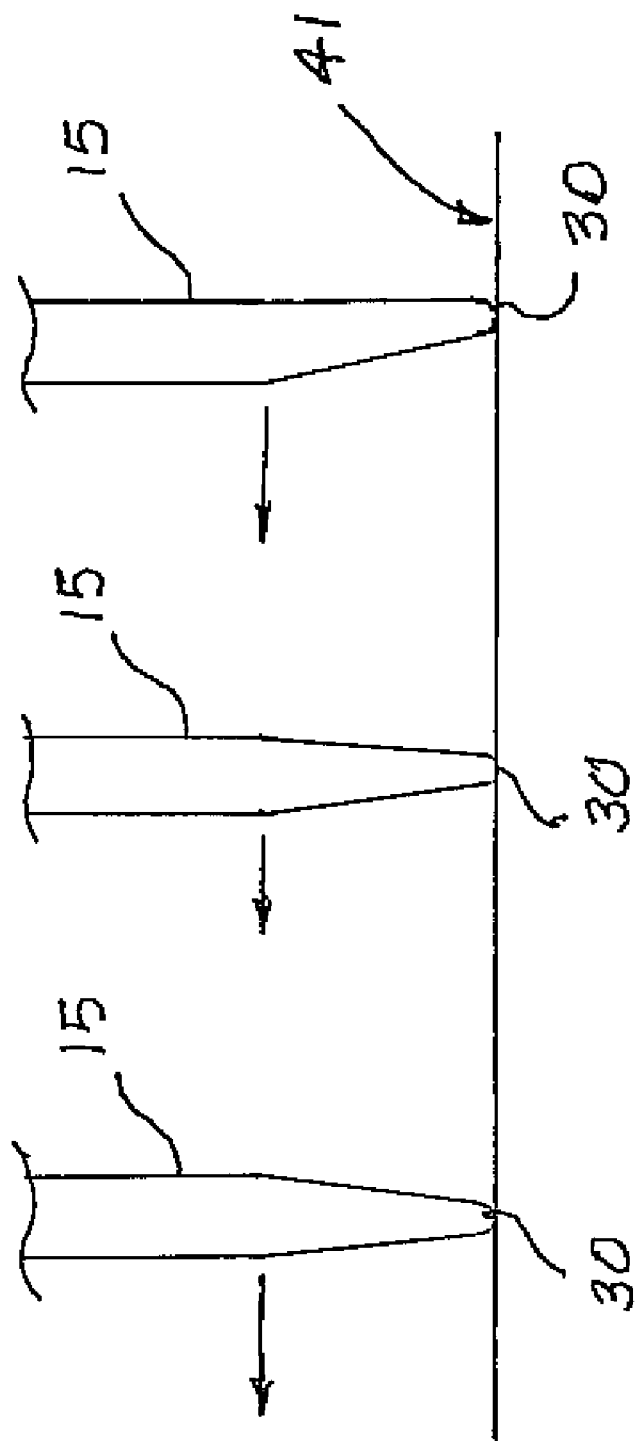
FIG. 5 shows partial side views of the blade in contact with the tongue surface, wherein a lower portion of the blade is shown illustrating blade flexing with, from left to right in the illustration: light, medium and heavy downward pressure and drag applied to the blade tip during scraping.

The scraping portion 18, along the curvilinear edge, terminates at a blade tip 30 that has an approximately circular circumference of at least 0.005 inches in radius. It has been found that such a tip is able to effectively scrape the tongue while not being able to damage the tongue, by cutting it, for instance. The blade 15 has a certain amount of flexibility due to the nature of the material of which it is made, preferably rubber, or a rubber-like substance. The material has a hardness of between 70 A and 80 A on the Shore A hardness scale. Therefore, the blade tip 30 tends to flex slightly when encountering compressive and drag forces during typical usage as will be described. This is illustrated in FIG. 5.

Figure 4:
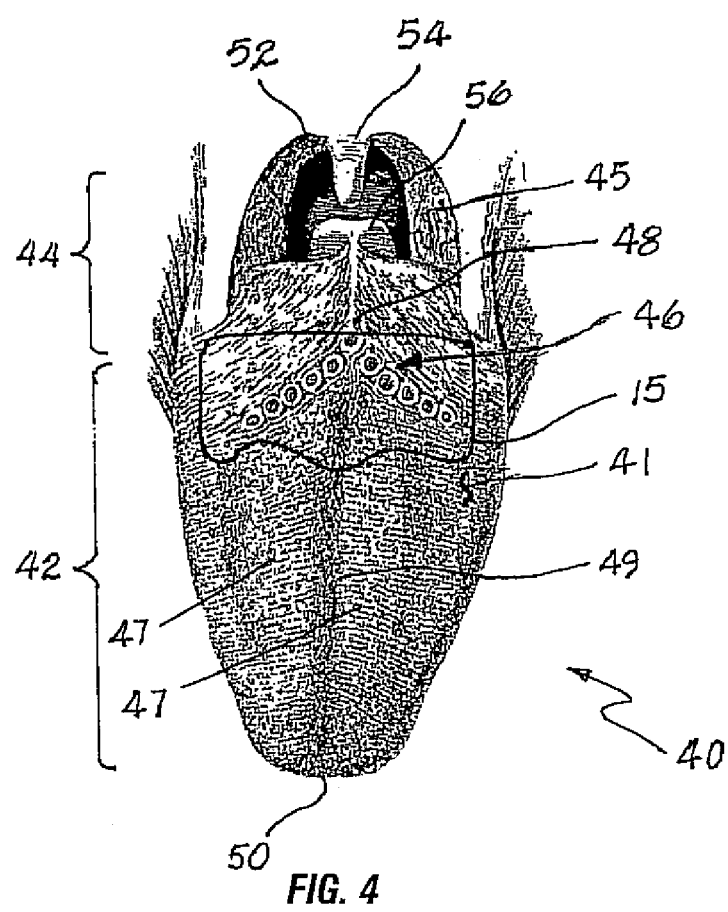
FIG. 4 is a top plan view of an adult human tongue illustrating intrinsic and extrinsic muscles thereof as well as surrounding tissues, and further showing an outline of the blade indicating its location for initiating a scraping action over the top surface of the tongue.

Before describing the manner in which the present invention is used, we now refer to FIG. 4, a view of the top surface (dorsum 41) of the human tongue 40. It is necessary to understand some of the characteristics of the human tongue 40, and especially the dorsum 41 and the intrinsic muscles 47 below the dorsum 41 in order to fully understand the utility of the invention. The human tongue 40 is a highly mobile, muscular structure vital for the digestive functions of chewing, taste, and swallowing. It is also important in speech, being essential for the proper production of all vowels and most consonants. The tongue 40 is made mainly of skeletal muscle and may be considered to have a freely moveable oral part 42 with which we all are familiar, and which, at rest, lies horizontally within the mouth. A fixed pharyngeal part 44 of the tongue faces backward to the oropharynx 52 and is comprised of lymphoid tissue and the lingual tonsil 45. These two parts 42 and 44 of the tongue 40 may be considered to be separated by a V-shaped furrow 46 defined by circumvallate papilla with its apex directed posteriorly. A pit 48 at the apex marks the site of the origin of the thyroglossal duct which, in the embryo, gives rise to the thyroid gland. The dorsum 41 is covered with various papillae, most of which are studded with taste buds. The mucous membrane covering the tongue 40 is continuous with that of the floor of the mouth (not shown) and also the oropharynx 52. The muscles of the tongue 40 are grouped into those which change its shape, called the intrinsic muscles, and those which change its position within the mouth, the extrinsic muscles. FIG. 4 also shown the locations of the uvula 54 and the epiglottis 56.

Since the tongue 40 contains no interior bony supports for its muscles, it is an example of a muscular hydrostat, similar in concept to an octopus' arm. The extrinsic muscles of the tongue anchor the tongue firmly to the hyoid bone, mandible, soft palate, and other surrounding structures. These attaching extrinsic muscles are in contrast to the intrinsic muscles of the tongue which lie entirely within the tongue structure. As shown in FIG. 4 the primary intrinsic muscles are the two longitudinalis linguae superior 47 which lie side-by-side and extend from the V-shaped furrow 46 to the tip 50. These two muscles (47) dominate the oral part 42 and principally determine the surface contour of the dorsum 41. It is noted that between the two linguae superior 47 lies a linear depression 49 extensive over the length of the oral part of the tongue 42.

The blade 15 is ideally adapted for cleaning the human tongue, and it can be modified for use with other primates, as well as animals of certain other species. In use, the blade tip 30 is placed in transverse contact with the dorsum 41 at the furthest posterior position possible as illustrated in FIG. 4. This posterior position varies with each individual as the gag reflex is triggered more easily with some persons. Once the blade 15 is in position and pressed against the dorsum 41, it is drawn toward the tip of the tongue 50. This process may be repeated to assure that the tongue is fully cleaned, however the invention is so effective that a single swipe of the tongue is generally sufficient.

The prior art teaches a blade similar to that of the invention, as for instance in Baker Des. 367,707. However, the Baker blade has a linear contact edge as shown in Baker FIGS. 3, 4 and 7, and this edge comes to an extreme point as shown in Baker FIGS. 5 and 6. Such an extreme point is dangerous as it is able to cut the dorsum 41 if the blade is drawn in any direction other then lateral to the blade's surface. Also, the fact that this blade is flat instead of curvilinear renders it somewhat ineffective. For instance, without considerable downward pressure of the edge on the tongue, debris within the linear depression 49 is not easily captured or removed.

In contrast, the concave segments 21, 22 of the curvilinear edge of the invention are spaced apart to approximately coincide with the two linguae superior 47 of the adult tongue and the convex segment 20 is therefore positioned over the linear depression 49. When pressed against the dorsum 41 and drawn forward, the linguae superior 48 are pressed slightly apart by the convex segment 20 thereby flattening the surface of the linear depression 49 and enabling the convex segment 20 to more fully engage the surface and scrape away debris.

The round edge of the tip 30 eliminates the possibility of cutting the dorsum 41 or otherwise damaging it. The width of blade 15 is approximately equal to the width of the adult human tongue, as shown in FIG. 4, so that typically a single scraping from back to tip is necessary for an effective result leaving the tongue clean.

The circular segments 23 and 24 are positioned at each end of the curvilinear edge and provide safety during use of the invention, as these corners of the blade 15, being rounded, are not able to scratch the dorsum 41. It is noted that the prior art blade of Baker (FIGS. 3 and 4) has sharp corners.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. An anatomically correct tongue scraping tool for use on the tongue, the tool consisting of:
   a blade holder mounted at one end of an elongated handle;
   a planar blade selectively and rigidly engaged with the blade holder, the blade having a width approximating the width of the human tongue;
   a scraping portion of the blade extending outwardly from the blade holder and terminating with a smoothly integrated curvilinear edge extending over the width of the blade;
   the curvilinear edge having curve segments limited to:
      a) two spaced apart, concave segments;
      b) a single convex segment; and
      c) two spaced apart, rounded segments joining the curvilinear edge with sides of the blade;
   wherein, the convex segment separates the concave segments and is positioned medially on the curvilinear edge; and
   the curvilinear edge approximating the transverse contour of the dorsum of the human tongue.

2. The anatomically correct tongue scraping tool of claim 1 wherein the concave segments of the curvilinear edge of the scraping portion are spaced apart to approximately coincide with superior longitudinal intrinsic muscles of the tongue.

3. The anatomically correct tongue scraping tool of claim 1 wherein the blade is made of a flexible material having a hardness between 70 A and 80 A on the Shore A hardness scale, wherein, the curvilinear edge of the blade is thereby adapted to flex when dragged on the tongue in contact with the dorsum.

4. The anatomically correct tongue scraping tool of claim 1 wherein a tip of the blade has an approximately circular form of at least 0.005 inches in radius.

5. The anatomically correct tongue scraping tool of claim 1 wherein the curvilinear edge approximately spans the width of an average tongue when the tongue is in a relaxed state.

* * * * *